(12) United States Patent
Mayer et al.

(10) Patent No.: US 11,931,284 B2
(45) Date of Patent: Mar. 19, 2024

(54) MULTI-DIGIT BRACES AND METHODS OF USE

(71) Applicant: Fight Fingers, LLC, Longmont, CO (US)

(72) Inventors: Christopher D. Mayer, Longmont, CO (US); David Z. Tusek, Longmont, CO (US); Rodney E. Ward, Longmont, CO (US)

(73) Assignee: FIGHT FINGERS, LLC, Longmont, CO (US)

( * ) Notice: Subject to any disclaimer, the term of this patent is extended or adjusted under 35 U.S.C. 154(b) by 1271 days.

(21) Appl. No.: 16/169,909

(22) Filed: Oct. 24, 2018

(65) Prior Publication Data

US 2019/0117438 A1    Apr. 25, 2019

Related U.S. Application Data

(60) Provisional application No. 62/576,519, filed on Oct. 24, 2017.

(51) Int. Cl.
*A61F 5/058* (2006.01)
*A61F 5/01* (2006.01)

(52) U.S. Cl.
CPC .......... *A61F 5/05875* (2013.01); *A61F 5/013* (2013.01); *A61F 2005/0197* (2013.01)

(58) Field of Classification Search
CPC .... A61F 5/05875; A61F 5/013; A61F 5/0118; A61F 5/10; A61F 5/019; A61F 5/105; A61F 5/05866; A61F 5/05858; A61F 5/05841; A61F 5/058; A61F 5/05; A61F 5/04; A61F 5/0102; A61F 5/0104; A41D 13/08; A41D 13/081; A41D 13/082; A41D 13/084; A41D 13/05; A41D 13/087; A44C 9/0023; A44C 9/00; A44C 9/0007; A44C 9/0015; A44C 9/0076; A44C 9/003

(Continued)

(56) References Cited

U.S. PATENT DOCUMENTS 2,471,997 A * 5/1949 Baltor ..................... A61F 5/019
    132/73
3,189,025 A * 6/1965 Yaklin ....................... A61F 5/10
    601/40

(Continued)

*Primary Examiner* — Michelle J Lee
*Assistant Examiner* — Robin Han
(74) *Attorney, Agent, or Firm* — Jason P. Webb; Pearson Butler (57) ABSTRACT

A brace and kit of braces with a method of use. The multi-digit brace includes first and second arcuate members coupled together by top and bottom bridge members. There are raised rails disposed about the circumference of the brace that form a band track within which an elastic band may be disposed to secure the brace to the fingers/toes of a hand/foot. The arcuate members are thinner near the bottom to allow for greater flex/bend of adjacent joints. The arcuate members are spaced from each other and form an hourglass shaped void therebetween. The arcuate members may form complete circles or may have gaps. The kit may include a plurality of braces and a plurality of bands/wraps/straps. The method includes installing a plurality of braces so that they face back-to-back towards a middle joint with thinner regions of each brace near the palmar side of the middle joint.

17 Claims, 11 Drawing Sheets

(58) Field of Classification Search
USPC .................. 602/22, 30, 11, 3; 128/893; 2/20
See application file for complete search history.

(56) References Cited

U.S. PATENT DOCUMENTS

| | | |
|---|---|---|
| 3,348,541 A | 10/1967 | Loebeck |
| 3,513,842 A | 5/1970 | Keenan |
| 3,943,922 A * | 3/1976 | Umeda .................... A61F 5/019 602/31 |
| 4,270,528 A | 6/1981 | Hanson |
| 4,674,487 A | 6/1987 | Schaeffer |
| 4,905,320 A | 3/1990 | Squyers, Jr. |
| 4,932,396 A | 6/1990 | Garris |
| 5,517,692 A | 5/1996 | Wunderlich-Kehm |
| 5,683,354 A | 11/1997 | Levy |
| 5,879,771 A | 3/1999 | Kypreos |
| 5,939,339 A | 8/1999 | Delmore et al. |
| 6,110,136 A | 8/2000 | Belkin |
| 6,932,782 B2 | 8/2005 | Ferraioli |
| 7,169,121 B2 | 1/2007 | Berrehail |
| 7,249,385 B2 | 7/2007 | Schukraft |
| 7,704,219 B2 | 4/2010 | Nordt, III et al. |
| 2007/0021700 A1* | 1/2007 | Liebowitz ................ A61F 5/10 602/22 |
| 2007/0276304 A1* | 11/2007 | Greenberg .......... A61F 5/05875 602/21 |
| 2010/0016771 A1 | 1/2010 | Arbesman et al. |
| 2012/0289877 A1 | 11/2012 | Hegland |
| 2013/0167282 A1 | 7/2013 | Ramirez |
| 2013/0281902 A1* | 10/2013 | McCrae ................ A61F 5/0118 602/22 |
| 2014/0079900 A1 | 3/2014 | Ramirez |
| 2015/0313327 A1* | 11/2015 | Ruppli .................. B32B 37/142 63/15 |

\* cited by examiner

MULTI-DIGIT BRACES AND METHODS OF USE

CROSS-REFERENCE TO RELATED APPLICATIONS

This invention claims priority, under 35 U.S.C. § 120, to the U.S. Provisional Patent Application No. 62/576,519 by Mayer et. al filed on Oct. 24, 2017, which is incorporated by reference herein in its entirety.

BACKGROUND OF THE INVENTION

Field of the Invention

The present invention relates to protective devices for fingers and toes, specifically to multi-digit braces that are used to support an injured finger or toe by coupling to an adjacent digit.

Description of the Related Art

Finger and toe (digits or phalanges) injuries are fairly common in various sports, especially in sports like basketball and baseball as well as combat sports (e.g. contact sports, martial arts, jiu-jitsu, wresting, mixed martial arts (hereafter referred to as MMA), grappling, judo and other dynamic activities where relatively fine manipulation of the fingers are required to perform well in the sport. Often a finger/toe of the hand/foot will be slightly misaligned during execution of a move, strike, or other action and that digit will then suffer a sprain, dislocation, fracture or other injury, while the surrounding fingers/toes are unhurt. There are also case where injury or disease may cause difficulty with a digit, such as but not limited to chronic arthropathy and various forms of arthritis, synovitis, enthesopathy, and tendinopathy; as well as post-surgical situations involving the hands and feet.

In such cases, it is often very helpful to brace the injured digit in some manner to protect against future injury, reduce pain and/or swelling, or to otherwise help the injured digit heal. Accordingly, various devices and techniques have been developed to brace injured digits, including but not limited to splints, wraps, and the like.

One such technique is to perform a syndactyl type procedure where one temporarily and reversibly affixes the injured digit to one or more adjacent digits for support. The procedure is also used in therapy unrelated to sports injuries, such as but not limited to some inflammatory conditions, as well as injuries not related to sports, such as those suffered on the job or otherwise. In many cases, this support is enough to allow the injured person to continue or return to the activity that may have spawned the injury, e.g. their sports performance. This procedure may also speed the healing of the digit where it is continued after the activity.

In the simplest case, the procedure is performed by wrapping sports wraps or athletic tape around the combined adjacent digits (often called "buddy taping"). In other cases, various splints and the like may be incorporated to provide a stable coupling of the adjacent digits that helps protect the injured digit from further injury.

In regards to finger splints, wraps and the like that are used to assist with digit injuries, improvements have been made in the field. Examples of references related to the present invention are described below in their own words, and the supporting teachings of each reference are incorporated by reference herein:

U.S. Pat. No. 4,674,487, issued to Schaeffer, discloses a helical band to be positioned around the second knuckle of the middle finger of the barber's hand which is not used to operate scissors. The band is used when cutting the ends of hair gripped between the index finger and the middle finger and prevents the scissors from cutting the flesh around the second knuckle.

U.S. Pat. No. 6,110,136, issued to Belkin, discloses a digit splint is defined by an arcuate angularly inclined base and an ovoid which extends upwardly and radially outward from the base. The base is positioned on the palmar side of a joint of a digit and the ovoid conforms to the dorsum of a digit when the digit is in an extended position without hyperextension. The ovoid has two substantially parallel sides which, when worn, conform to impinge on the sides of the joint of a digit at the axis to provide lateral stability at the joint of a digit and to prevent migration of the splint on a digit. The splint also prevents hyperextension of the joint of a digit. In an alternate configuration, the splint may be rotated 180 degrees about the horizontal axis on a joint of a finger. In this configuration, the splint provides lateral stability at a joint of a digit and corrects flexion at a joint of a digit.

U.S. Pat. No. 6,932,782, issued to Ferraioli, discloses a device for limiting movement of a joint. Once prepared, the device includes two tubular openings for encircling phalanxes on either side of the joint. The tubular sides are attached by a portion of the device that can cover either the top portion of the joint or the underside of the joint. This configuration allows an individual to flex the joint in a limited manner.

U.S. Pat. No. 7,169,121, issued to Berrehail, discloses a medical device for syndactyly of at least two fingers or toes, said device being in one piece and comprising at least two rings joined via at least one connection bar in such a way as to permit sliding of the syndactylized fingers or toes relative to one another.

U.S. Pat. No. 7,249,385, issued to Schukraft, discloses a finger/toe tip protective apparatus including a semispherically shaped flexible member of perforated material with inner and outer surfaces, and a circumferential edge. The flexible member has at least one elongated tab extending tangentially and radially about the circumferential edge of the member and which, when wrapped about the digit is partially secured to both the circumferential edge of the member and the skin of the digit to which the apparatus is to be secured whereby allowing the protective apparatus to be releasably secured in position on the finger/toe tip of a person.

U.S. Patent Application Publication No. 2012/0289877, by Hegland, discloses ring splint that includes a first loop, a second at least partial loop, an elongated support and optionally a third at least partial loop, the first loop and the second at least partial loops being attached to the elongated support such that the elongated support contacts the ventral surface (e.g., palmar or plantar) of a phalange (e.g., finger or toe) when in position on a phalange.

The inventions heretofore known suffer from a number of disadvantages which include requiring two-hands to install, needing tape/wrap to apply, not designed to apply as a reusable, standalone product without tape, being difficult to apply, being uncomfortable, not allowing for a full range of motion (hereafter referred to as ROM), not allowing one to be active during a recovery period, not protecting from lateral force, not protecting from torsional or rotational force, being heavy, being bulky, being made from rigid materials, not promoting healing, limiting ROM and thereby leading to over-immobilization of a joint, not preventing re-injury, not being usable in sporting, training, and competitive environments, not being designed to limit injury to others in activity and with contact, not being designed to fit the contour of the fingers, not designed to function on a digit while joint is in motion, not conforming and accommodating the varying biomechanic and ergonomic forces present during functional ROM, not being designed to stay applied during activity and contact, not allowing full use of hand/fingers/digits, not allowing gripping, flexion, extension, and full dexterity of the digits; not allowing mobility in a healing finger/joint, not utilizing the finger next to it for support, not offering the option apply unilaterally or bilaterally to address protection on one or both sides of the knuckle/finger, not being designed to protect and prevent specific ligament & joint injuries, not being designed to be sufficiently mobile, flexible, and malleable to allow dexterity, adequate use and ROM of the digits, not being designed to protect and prevent injuries from specific forces and events in combat and sporting situations, not being designed to create a functional space between the fingers for dexterity, not being designed to create space between the fingers to prevent re-injury, and eliminate irritation and pressure on the lateral surface of the knuckle; not being designed to protect singularly the proximal or distal knuckle of the finger, or either or both simultaneously; and/or not enabling an earlier return to work, sport, or when manual dexterity is requisite.

What is needed is a multi-digit brace and/or method of use thereof that solves one or more of the problems described herein and/or one or more problems that may come to the attention of one skilled in the art upon becoming familiar with this specification

SUMMARY OF THE INVENTION

The present invention has been developed in response to the present state of the art, and in particular, in response to the problems and needs in the art that have not yet been fully solved by currently available multi-digit braces. Accordingly, the present invention has been developed to provide a multi-digit brace, kit, and method of use thereof.

According to one embodiment of the invention, there is a multi-digit brace that includes a first arcuate member and a second arcuate member. The second arcuate member may be coplanar to and/or coupled to the first arcuate member. Such may be effected by a top bridge member that may couple a top region of the first arcuate member to a top region of the second arcuate member and/or a bottom bridge member that may couple a bottom region of the first arcuate member to a bottom region of the second arcuate member. It may be that the bottom region of each of the first and second arcuate members is thinner front-to-rear than the thickness of the top region.

There may also be a band track extending about one or more of the top region, the bottom region, a left side region, and/or a right side region of the first and second arcuate members. The track may bounded by a first raised barrier that may extend from and.or may be coplanar to a front face of the brace and/or may be bounded by a second raised barrier that may extends from and/or may be coplanar to a rear face of the brace at the top region. There may be an elastic band that may be removably coupled about the band track and/or elastically secured thereto.

It may be that the second arcuate member is spaced from the first arcuate rem r be Such spacing may form an hourglass-shaped void between the first arcuate member and the second arcuate member.

It may be that neither of the first arcuate member and the second arcuate member form a complete circle, thereby leaving a first gap between edges of the first arcuate member and a second gap between edges of the second arcuate member. It may be that one or both of the first and second arcuate members form a complete circle.

It may be that a gap of the first annular member is disposed about a boundary between a right side region and the bottom region and/or a gap of the second annular member is disposed about a boundary between a left side region and the bottom region.

In another non-limiting embodiment, there is a multi-digit brace kit. The kit may include one or more braces as described herein and/or may include one or more elastic bands as described herein.

In yet another nonlimiting embodiment, there is a method of bracing a set of adjacent digits. The method include the steps of: inserting a first digit into a first arcuate member of a first brace; inserting a second digit into a second arcuate member of the first brace, wherein the second arcuate member is coplanar to, spaced from, and coupled to the first arcuate member by a top bridge member coupling a top region of the first arcuate member to a top region of the second arcuate member; and a bottom bridge member coupling a bottom region of the first arcuate member to a bottom region of the second arcuate member; and/or positioning the first brace such that a rear face of the first brace, which rear face has a narrowed portion, front-to-back, compared to a front face thereof, towards an adjacent joint of the digit. Such may also include positioning a second brace on the first and second digits on an opposite side of the joint with a rear face having a narrowed, front-to-back, portion facing the rear face of the first brace, such that the joint is flanked by the first and second braces and the first and second braces are back-to-back. Such may also include disposing an elastic band about the first brace, the elastic band sized such that it elastically couples to the brace.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order for the advantages of the invention to be readily understood, a more particular description of the invention briefly described above will be rendered by reference to specific embodiments that are illustrated in the appended drawing(s). It is noted that the drawings of the invention are not to scale. The drawings are mere schematics representations, not intended to portray specific parameters of the invention. Understanding that these drawing(s) depict only typical embodiments of the invention and are not, therefore, to be considered to be limiting its scope, the invention will be described and explained with additional specificity and detail through the use of the accompanying drawing(s), in which.

DETAILED DESCRIPTION OF THE INVENTION

For the purposes of promoting an understanding of the principles of the invention, reference will now be made to the exemplary embodiments illustrated in the drawing(s), and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would occur to one skilled in the relevant art and having possession of this disclosure, are to be considered within the scope of the invention.

Reference throughout this specification to an "embodiment," an "example" or similar language means that a particular feature, structure, characteristic, or combinations thereof described in connection with the embodiment is included in at least one embodiment of the present invention. Thus, appearances of the phrases an "embodiment," an "example," and similar language throughout this specification may, but do not necessarily, all refer to the same embodiment, to different embodiments, or to one or more of the figures. Additionally, reference to the wording "embodiment," "example" or the like, for two or more features, elements, etc. does not mean that the features are necessarily related, dissimilar, the same, etc.

Each statement of an embodiment, or example, is to be considered independent of any other statement of an embodiment despite any use of similar or identical language characterizing each embodiment. Therefore, where one embodiment is identified as "another embodiment," the identified embodiment is independent of any other embodiments characterized by the language "another embodiment." The features, functions, and the like described herein are considered to be able to be combined in whole or in part one with another as the claims and/or art may direct, either directly or indirectly, implicitly or explicitly.

As used herein, "comprising," "including," "containing," "is," "are," "characterized by," and grammatical equivalents thereof are inclusive or open-ended terms that do not exclude additional unrecited elements or method steps. "Comprising" is to be interpreted as including the more restrictive terms "consisting of" and "consisting essentially."

FIGS. 1-6 show various views of a multi-digit brace, according to one embodiment of the invention. There is shown a first arcuate member 110 coupled to a second arcuate member 120 via a top bridge member 130 and a bottom bridge member 140. There are raised barriers 150, 152, 154 that form a hand track 156 about a perimeter of the brace 100.

The illustrated first arcuate member 110 mates with an exterior of a digit when the brace is installed thereon. It also serves as a barrier between the adjacent digits that are to be coupled together by the brace in a syndactyl type procedure. The arcuate member may be shaped as shown, but other embodiments include terminating the arc such that it is shorter (e.g. terminating the arc in other non-limiting positions such as those shown in FIG. 3 at positions 112, 114, 116, 118) or may extend as a complete circle as shown by dotted lines 119 in FIG. 3. The second arcuate member 120 may terminate or extend in a similar manner. Wherein the arcuate members do not form a complete circle, a convenient gap 122 (See FIG. 3) is left between the ends 124, 126 (See FIG. 3) thereof that allows for insertion of a digit, through the gap 122 without having to "thread" the digit through the arcuate member. The illustrated the gap 115 of the first annular member 110 is disposed about a boundary between a right side region 134 and the bottom region 142 and the illustrated gap 125 of the second annular member 120 is disposed about a boundary between a left side region 136 and the bottom region 142. It is understood that the gaps of the arcuate members may be disposed at different positions from those shown and that the gaps need not be symmetrical between the first and second arcuate members, even though, as shown, they are. Further, wherein the arcuate members terminate at different locations from those shown, the gaps may be larger and/or positioned differently than what is shown in the figures, or they may be non-existent wherein the arcuate members form complete circles. The illustrated gap(s) advantageously allow the accurate member radius/size to expand and contract to accommodate varying finger sizes.

The illustrated second arcuate member 120 is coplanar to, spaced from, and coupled to the first arcuate member 110 by the top bridge member 130 coupling a top region 132 of the first arcuate member to a top region 132 of the second arcuate member, and a bottom bridge member 140 coupling a bottom region 142 of the first arcuate member 110 to a bottom region 142 of the second arcuate member 120. Being coplanar, the first and second arcuate members, if extended as cylinders, are also parallel forms. In this manner, adjacent digits may extend through each without having to change their natural orientation.

The illustrated first and second arcuate members 110, 120 are spaced apart from each other and the spacing thereof and the top and bottom bridge members 130, 140 form an hourglass-shaped void 133 between the arcuate members 110, 120. This void 133 provides for enhanced flexibility of the brace and enhances the articulability of the adjacent digits enclosed thereby. This is particularly beneficial for basketball, baseball, and other activities where independent flexing and/or articulation of adjacent fingers is important to game play and performance (See, generally, FIG. 10).

The illustrated first and second arcuate members 110, 120 each include a thin region 160 and a thick region 162, wherein thin/thick is measured between the back face 164 and the front face 166. The illustrated thin region 160 is disposed at a bottom-side portion of each of the arcuate members. Wherein that thinner portion, when installed over a digit, is placed adjacent a joint where enhanced flexing/articulation is desired, the thinner region has reduced impedance of such flexing/articulation, without giving up the beneficial syndactyly effect. Accordingly, the bottom region of each of the illustrated first and second arcuate members is thinner front-to-rear than the thickness of the top region thereof. Looking at FIG. 3, the planar shape of the front face 166 is not distorted at the thinner region 160, while the rear face 164 is not planar at the transition region 163 between the thinner region 160 and the thicker region 162.

This difference in thickness provides enhanced operability of the hand on which it is disposed and allows for full clenching of the hand in grasping objects and/or making hand configurations (e.g. a fist) without discomfort or pinching the fingers. This asymmetry is a functional part of the design and causes the device to be directional. The illustrated device can be applied in two locations between two fingers, proximally between the hand and second knuckles on the most proximal phalanges to the hand, and distally between the two knuckles on the second most proximal phalanges to the hand. The thinner region, when applied, is designed to generally sit distal to the middle knuckle when installed on a hand. When applied proximal to the hand it sits in one direction, and when applied distally it is flipped in order to provide the functional benefits it was designed for, allowing full range of motion, as well as gripping and making a fist without pinching the fingers or pinching the device between the interior of the fingers where the finger bends.

The illustrated top bridge member 130 connects the first and second arcuate members 110, 120 about a top region thereof 132. The illustrated bottom bridge member 140 connects the first and second arcuate members 110, 120 about a bottom region thereof 142. Together, the top and bottom bridge members 130, 140 provide a stable connection between the spaced arcuate members 110, 120 such that digits disposed therein will be syndactyly coupled together for the benefit of one or more of such digits.

The illustrated raised barriers 150, 152, 154 in association with the adjacent surfaces about the perimeter of the brace form a band track 156 about which a band, strap, wrap, or other structure may be disposed to more firmly secure the digits within the arcuate members when installed on digits. The illustrated raised barriers (rails) are coplanar with the faces on which they appear, thereby not interrupting the profile thereof and resulting in easier manufacturing and storage as well is reducing surface properties that might be irritating or distracting to the wearer.

The illustrated band track 156 retains any band, wrap, strap, etc. into which such is placed so that the hand, wrap, strap, etc. is less likely to fall off or become displaced during use. The illustrated band tack 156 extends about the top region 132, the bottom region 142, the left side region 136, and the right side region 134 of the first and second arcuate members 110, 120. The band track 156 is bounded by a first raised barrier 150, 152 extending from and coplanar to a front face 156 of the brace 100 and is also bounded by a second raised barrier 154 that extends from and is coplanar to a rear face 154 of the brace 100 at the top region 132, thereof.

In operation, one places the adjacent digits within the arcuate members, positions the brace as desired on the digits and then disposes a wrap, band, strap, etc. about the brace to hold it in place. Where the brace includes one or more arcuate members that is a complete circle, then the appropriate sized brace must be selected to fit the digits, and the need for a band, wrap, or strap to apply the device may thereby be eliminated. Wherein the arcuate members include gaps, fewer sizes of braces are required to account for different sizes in digits.

Advantageously, the illustrated brace and various embodiments thereof described herein provides for one or more of the following benefits: bridges fingers for support and protection while allowing full range of motion of the joints; creates a natural and useful space between the fingers for healing; durable; reusable; replaces the need for disposable tape; offers superior support and protection over other braces/splints; decreases the risk of re-injury; offers improved comfort over taping; is quicker and easier to apply than buddy-taping; reduces irritation to existing injuries; reduces healing times; allows full use of the hand and range of motion of the fingers for flexion, extension, and gripping; allows individual finger dexterity while using the healthy neighboring finger as a functional anatomical splint; prevents lateral movement and other directional force unnatural to the hinge joint of the fingers; and/or allows active recovery and participation while healing.

Unlike a splint the illustrated device allows dexterity, flexion, extension, full use, gripping, first/striking (without pinching on the palm side), ball/racquet/club/stick/bat handling, full ROM, and ability to engage in activity while protecting injuries without harming other participants. The device prevents lateral, torsional, and unnatural movement, and force to the knuckle/hinge joint, provides protection, provides comfort, allows active recovery and promotes healing. The illustrated device creates a space between fingers so the injured surface (lateral side of knuckle) doesn't get irritated with contact of neighboring finger or get reinjured by impact in the lateral direction. The healthy neighboring finger provides structural support and protects the injured side of the healing linger by being positioned parallel to it. Like buddy taping the illustrated devices allow a healthy finger to protect and support a neighboring healing finger. Unlike buddy taping the illustrated devices provides a functional space between fingers that provides comfort, reduces irritation, promotes healing, protects existing injuries, prevents re-injury and new injuries, and allows better use, dexterity, independent finger movement, and ROM over buddy taping.

The illustrated device provides support and protection while allowing maximum ROM, gripping, flexion, extension, functionality, and dexterity of the knuckles, fingers and hands, even in an injured state. The device provides ease and efficiency of application and can eliminate the need for taping and re-taping digits during sports and activity. The device provides protection from injury and prevention of re-injury, and promotion of active recovery while healing injuries. The device is comfortable and utilizes a neighboring healthy digit tor support, without the limitations of taping and restricting finger by securing it directly to the neighboring finger.

Figure 1:
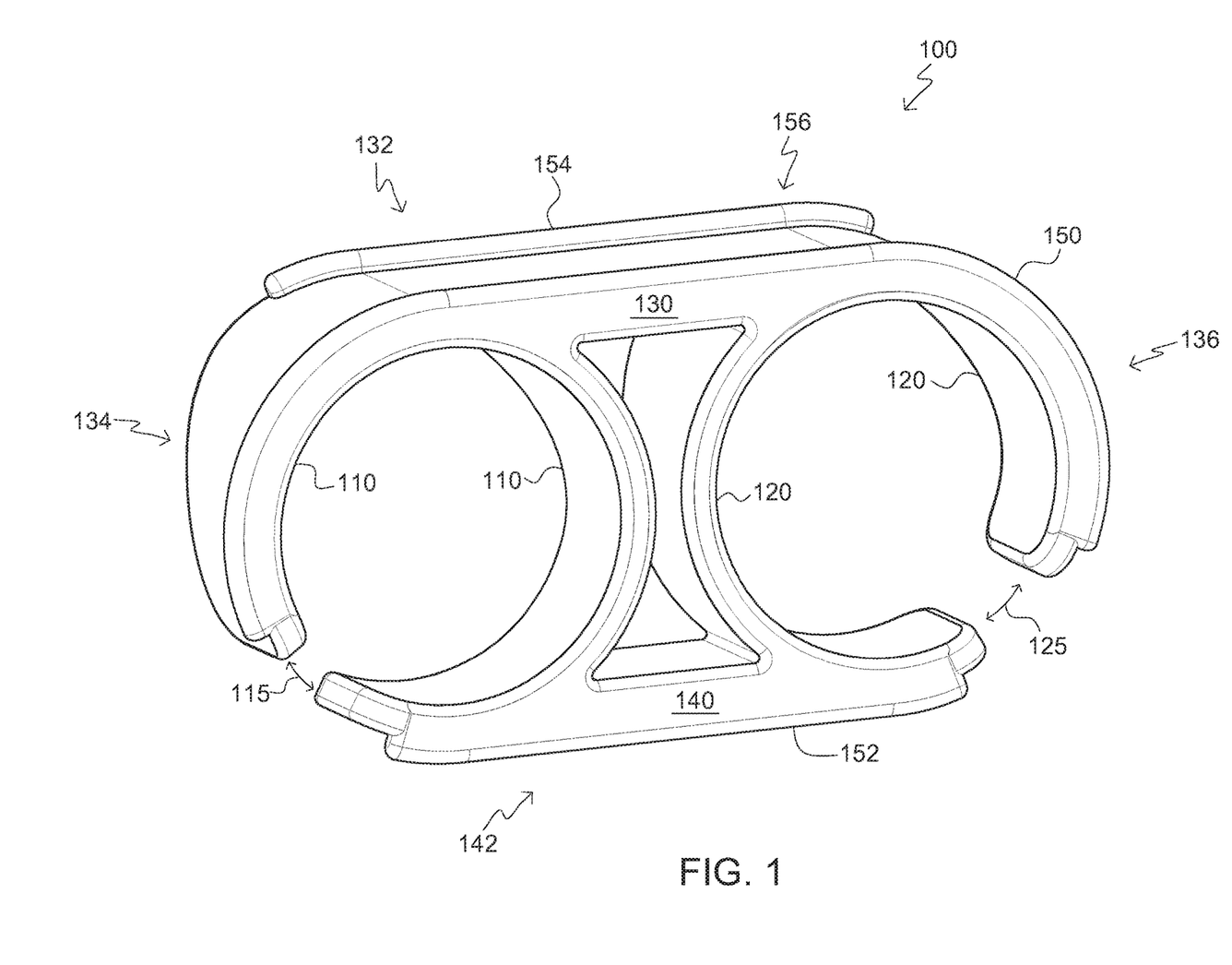
FIG. 1 is a front-top perspective view of a multi-digit brace, according to one embodiment of the invention.
Figure 2:
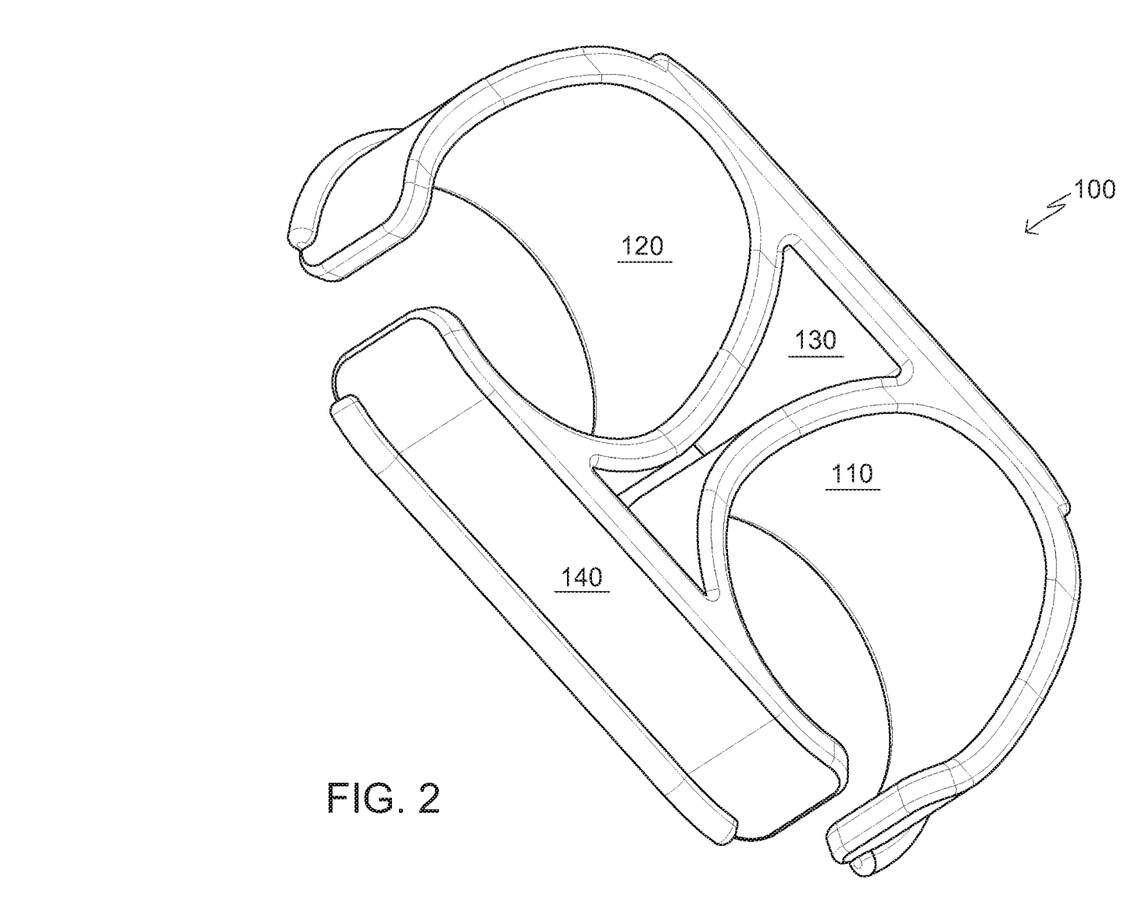
FIG. 2 is a rear-bottom perspective view of a multi-digit brace, according to one embodiment of the invention.
Figure 3:
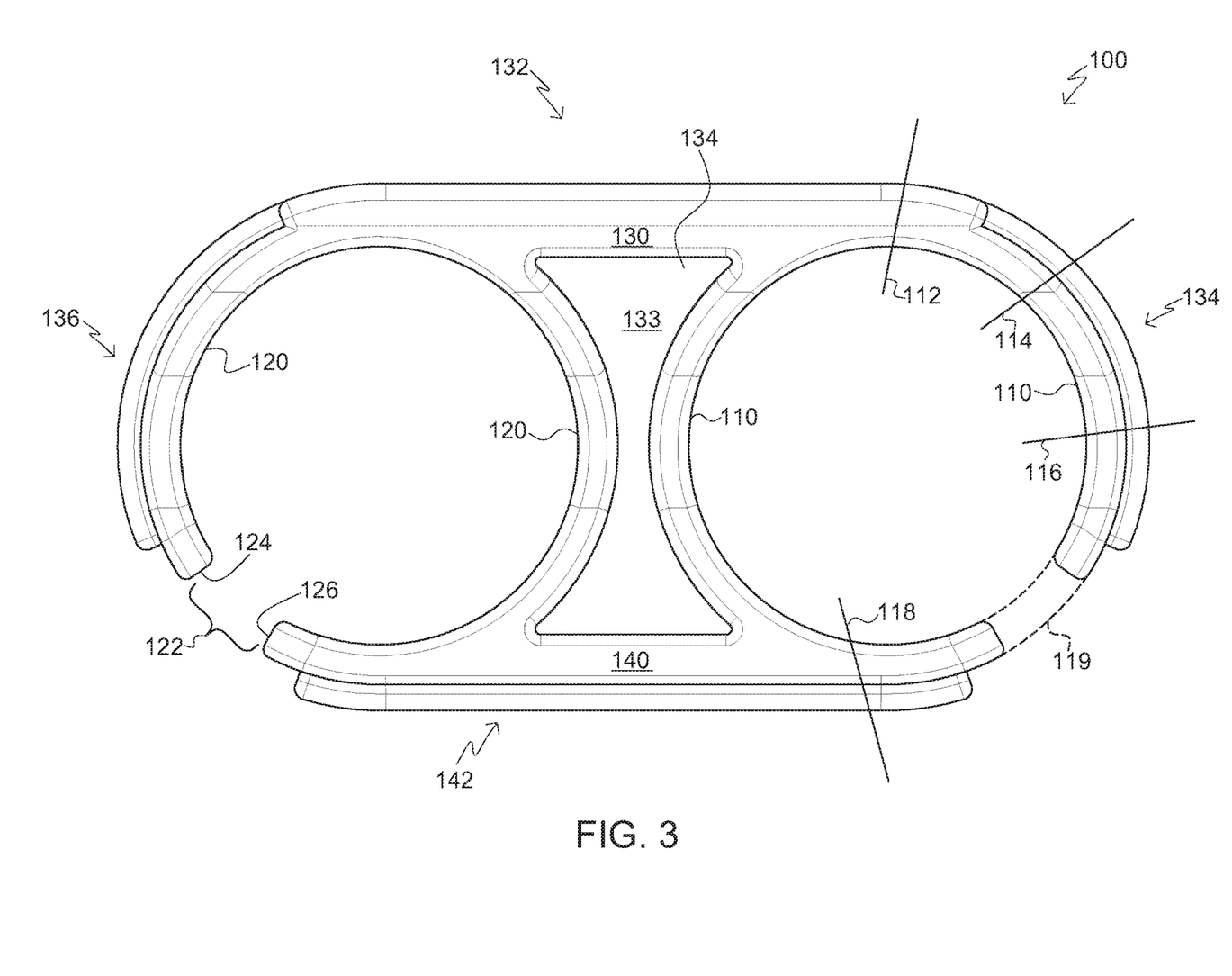
FIG. 3 is a rear elevational view of a multi-digit brace, according to one embodiment of the invention.
Figure 4:
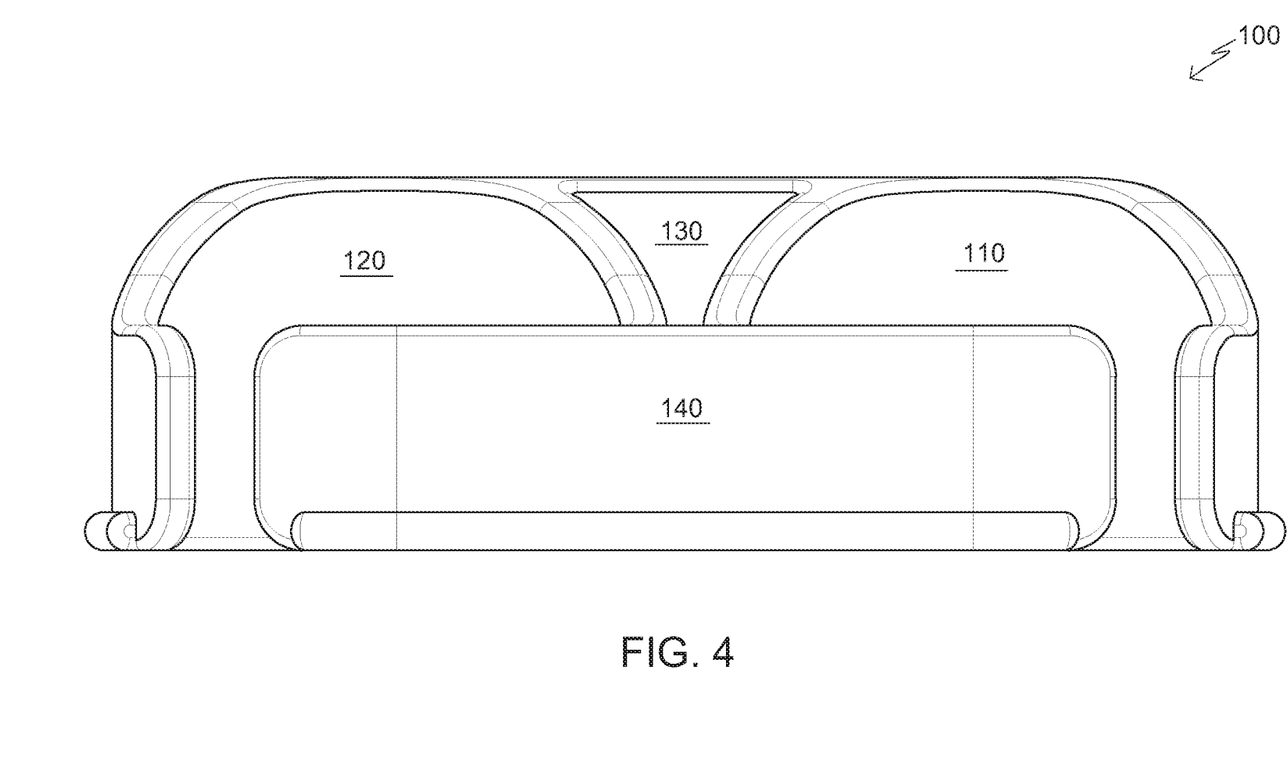
FIG. 4 is a bottom planar view of a multi-digit brace, according to one embodiment of the invention.
Figure 5:
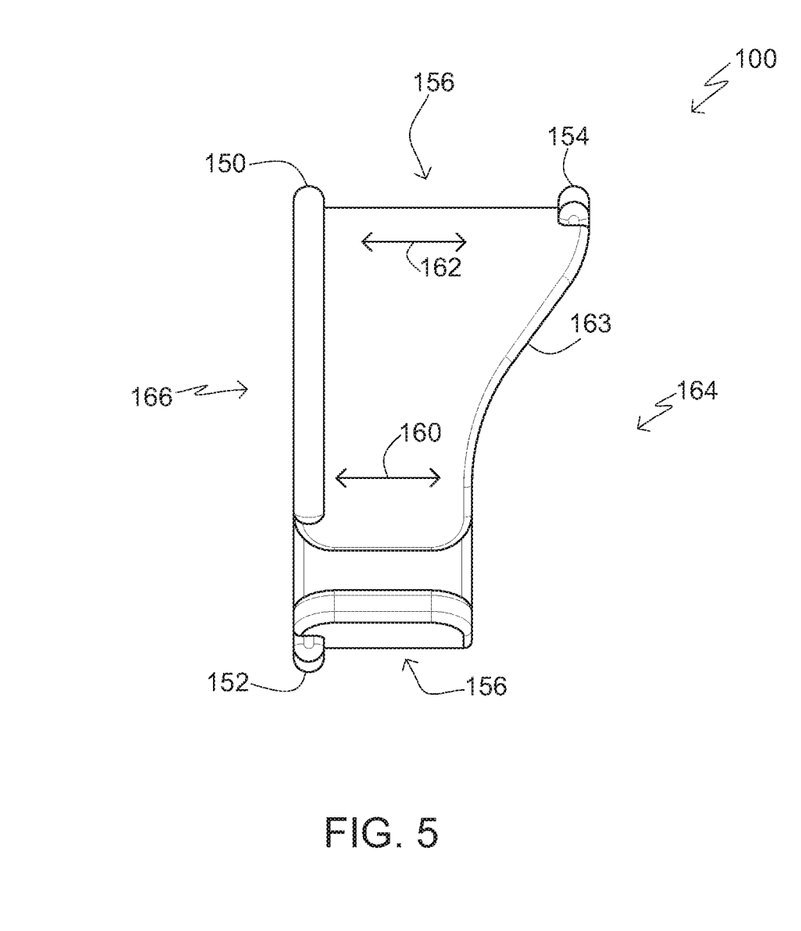
FIG. 5 is a left side elevational view of a multi-digit brace, according to one embodiment of the invention.
Figure 6:
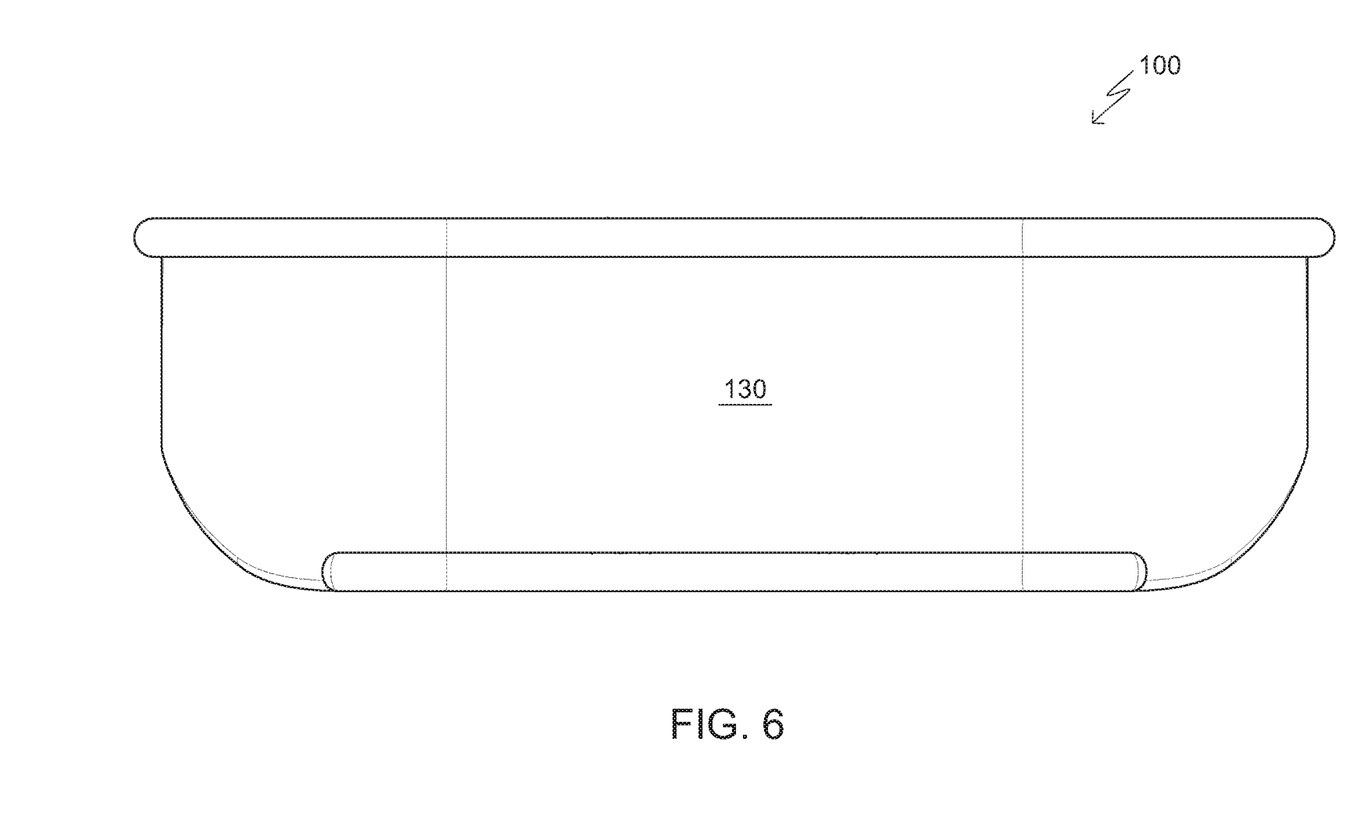
FIG. 6 is a top planar view of a multi-digit brace, according to one embodiment of the invention.
Figure 7:
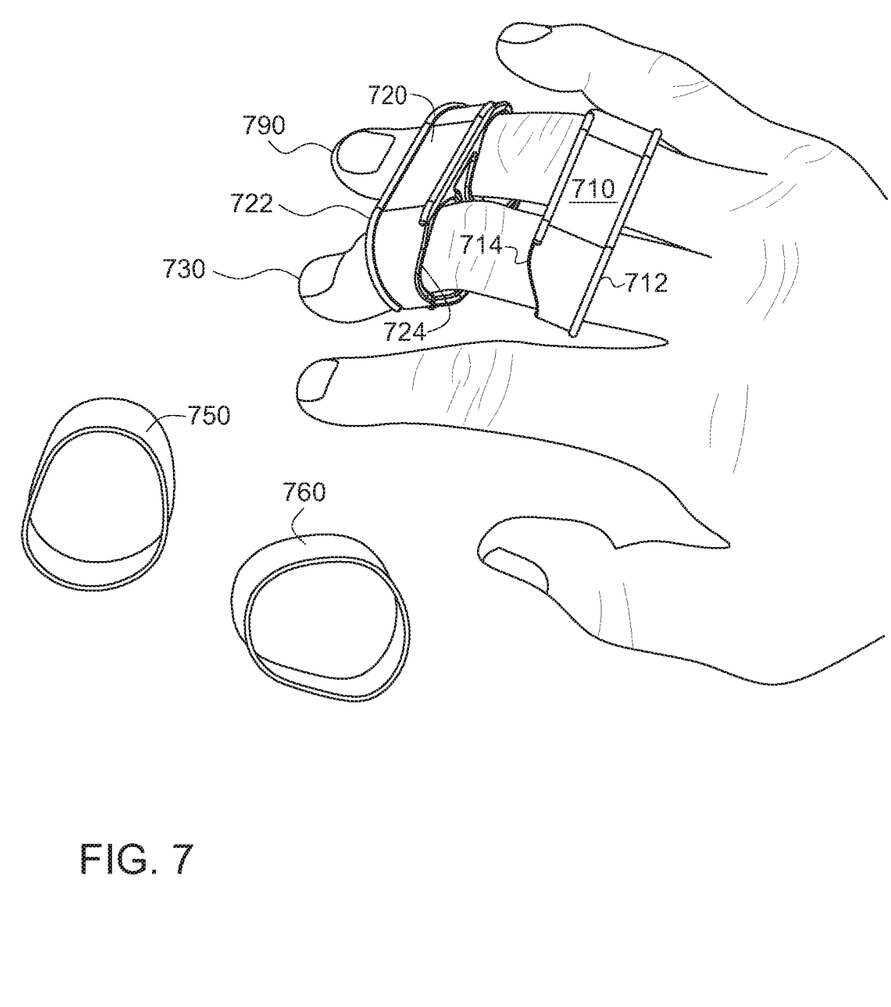
FIG. 7 is a perspective view of a pair of braces disposed back-to-back with respect to each other; flanking joints of a pair of fingers of a hand, with a pair of elastic bands disposed nearby, according to one embodiment of the invention.
Figure 8:
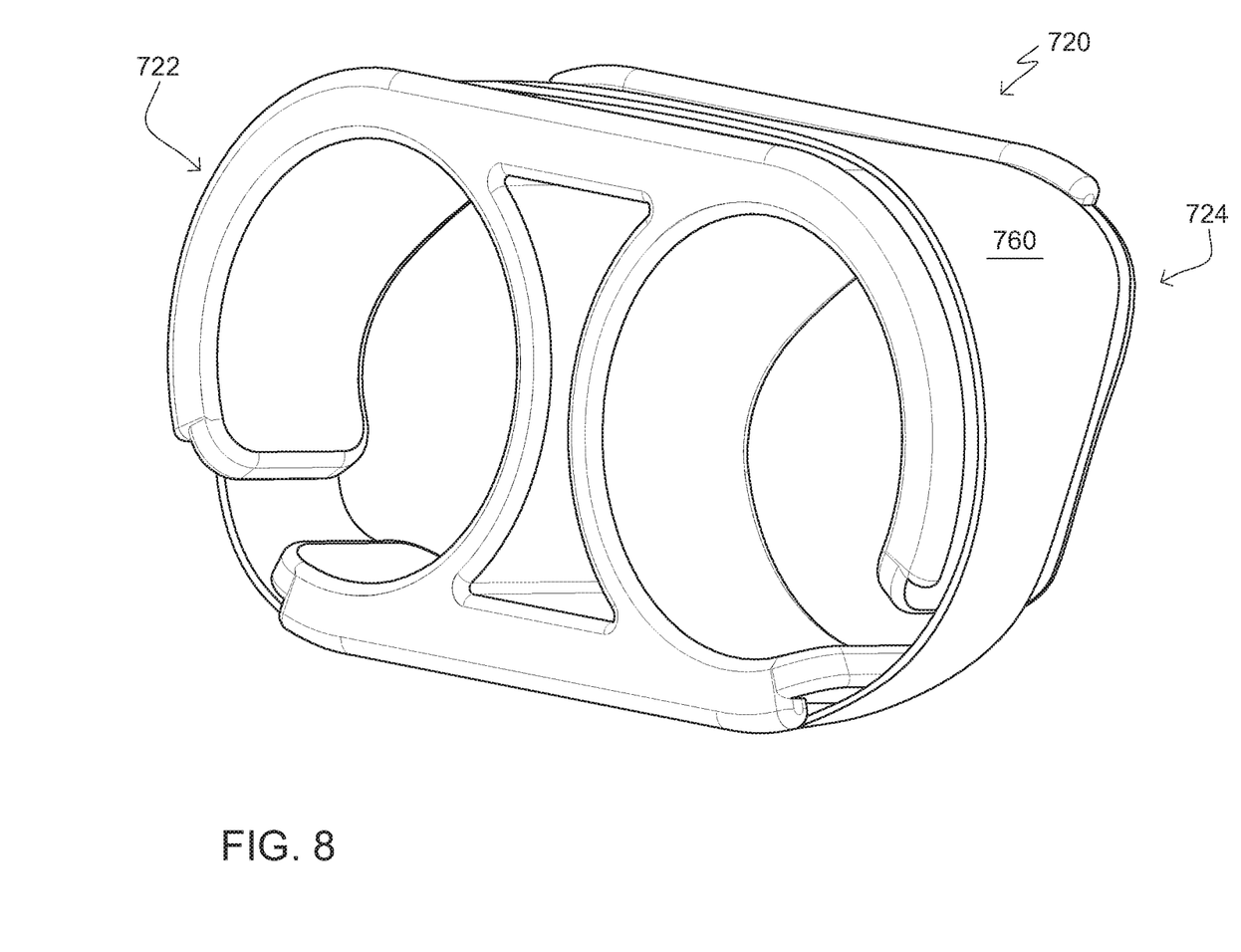
FIG. 8 is a front-left perspective view of a multi-digit brace having an elastic band disposed therearound and coupled thereto elastically, according to one embodiment of the invention.
Figure 9:
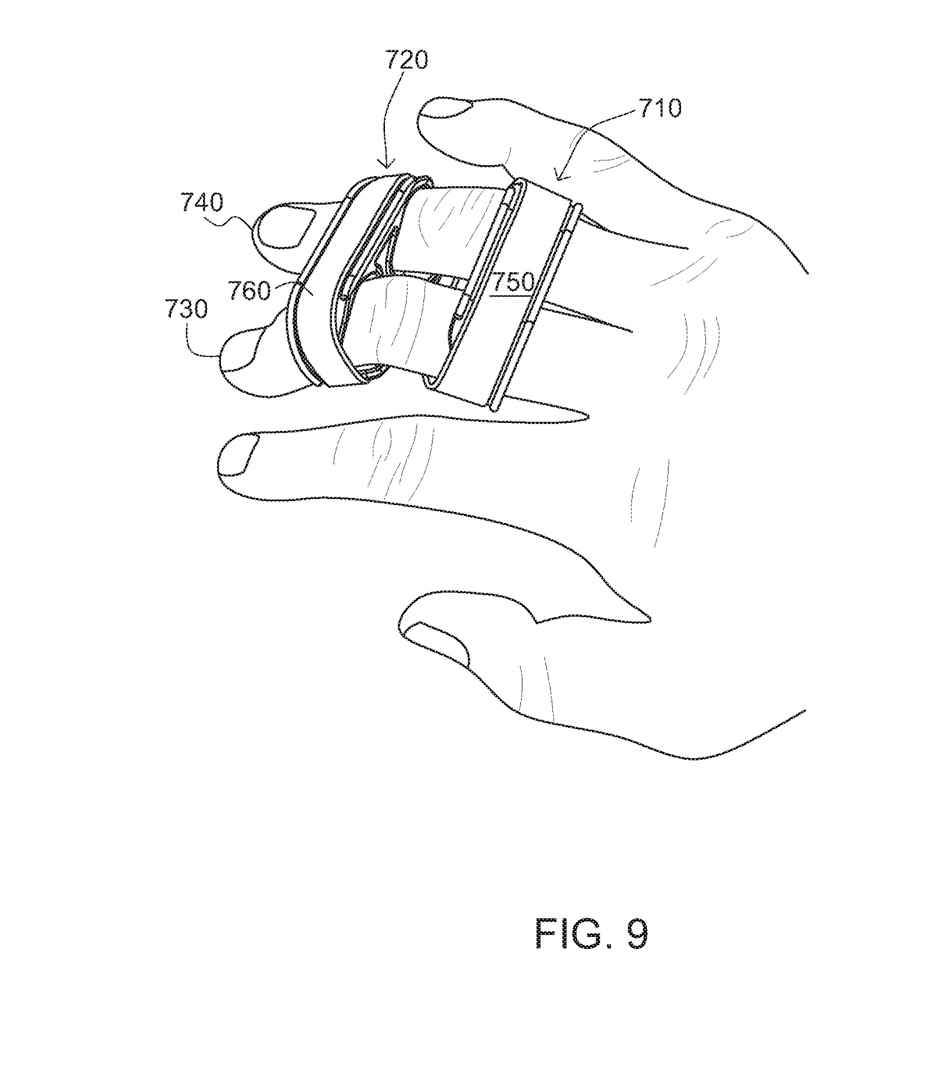
FIG. 9 is a perspective view of a pair of braces disposed back-to-back with respect to each other; flanking joints of a pair of fingers of a hand, with a pair of elastic bands disposed therearound and coupled thereto elastically, according to one embodiment of the invention.

Looking to FIGS. 7-9, there is shown a first brace 710 and a second brace 720 disposed about the middle finger 730 and ring finger 790 of a human hand, along with a pair of elastic bands 750, 760 adjacent thereto. The illustrated braces 710, 720 and bands 750, 760 may form a multi-digit brace kit.

The illustrated first brace 710 is disposed across the proximal phalanges if the fingers 730, 790 with the front face 712 of the first brace 710 facing the knuckles between the proximal phalanges and the metacarpals of the hand. The rear face 714 of the first brace 710 is facing the knuckles between the proximal phalanges and the intermediate phalanges, thereby also facing the rear face 724 of the second brace 720. As shown, the thinner palmar side region of the first brace is disposed adjacent the knuckle between the proximal phalanges and the intermediate phalanges near the palmar region thereof, which is the direction of pivot/bend that the knuckle takes when making a fist. This allows the knuckle a greater range of motion than would otherwise be allowed, while still providing a firm and stable support and coupling of the fingers.

The illustrated second brace 720 is flipped 180 degrees compared to the first brace, such that they are back-to-back with the rear of each facing each other and the rear of each facing the knuckle between the proximal phalanges and the intermediate phalanges. Accordingly, the front 722 of the illustrated second brace is facing out towards the fingertips. The second brace is disposed over the intermediate phalanges of the fingers 730, 790. The illustrated braces may include one or more plastics, rubbers, silicones, metals, fibers, ceramics, and the like. Generally, it is desirable for the braces to be a mix between rigid and flexible so that it is easy and comfortable to insert and position the digits but also so that the adjacent digits are held together in a stable and firm position. The materials for the braces will generally be selected to match up with desired operational characteristics and it is understood that any materials that meet the desired needs for comfort, stability, durability, cost, manufacturing ease, storage, etc. may be suitable to use with the braces and variations thereof described herein and that the specific compositions of such are expected to be plethoric.

The illustrated elastic bands 750, 760 are removably coupleable about the band tracks of the respective braces and are sized to be elastically secured thereto. Accordingly, the elastic bands have a natural circumference/length that is a little smaller than the circumference of the brace so that the elastic must stretch to go around the brace and thereby the biased or spring-like nature of the elastic holds the elastic tightly to the brace within the band track. Generally, the elastic bands include one or more rubbers, silicones, plastics and the like and combinations thereof such that they may be stretched to a different effective length/circumference hut then return to their original shape while not under force.

Figure 10:
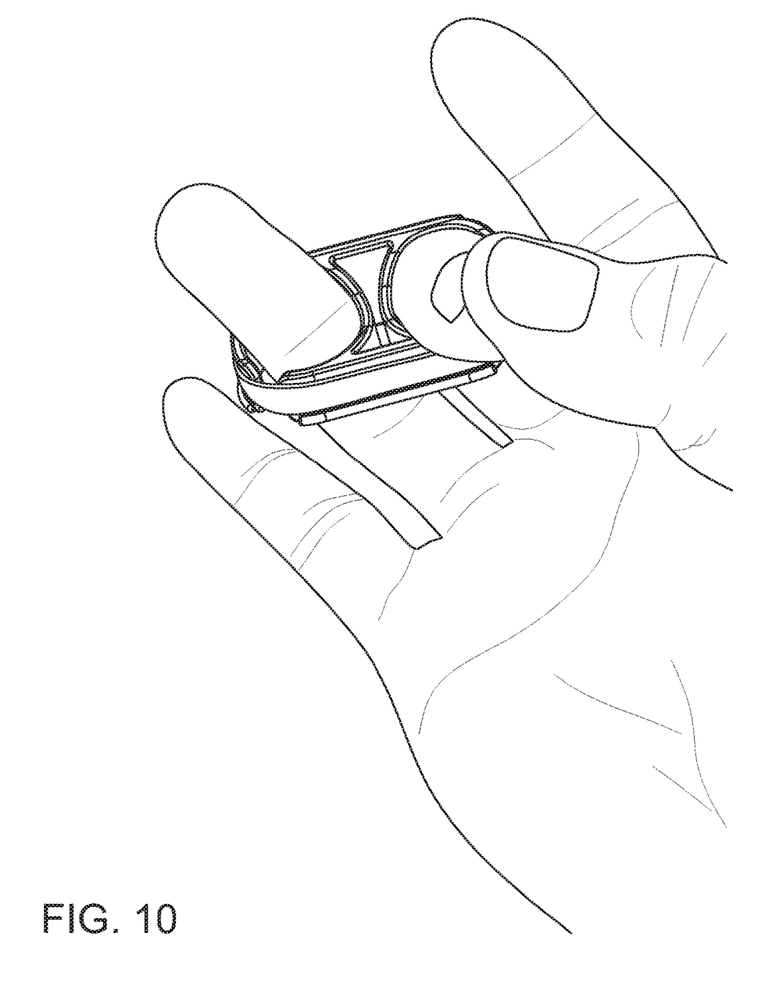
FIG. 10 is a perspective view of a brace disposed adjacent joints of fingers of a hand, with an elastic band disposed therearound and coupled thereto elastically, showing articulation of a joint thereof, according to one embodiment of the invention.

FIG. 10 is a perspective view of a brace disposed adjacent joints of fingers of a hand, with an elastic band disposed therearound and coupled thereto elastically, showing articulation of a joint thereof, according to one embodiment of the invention. The middle finger of the illustrated hand is flexed compared to the syndactyly coupled ring finger and is touching the thumb of the same hand, while the ring finger is extended. Accordingly, a great range of motion is allowed by the illustrated brace, while protecting the associated finger, helping such to heal as needed and allowing independent finger movement while still maintaining the connection and support of a healthy neighboring finger.

Figure 11:
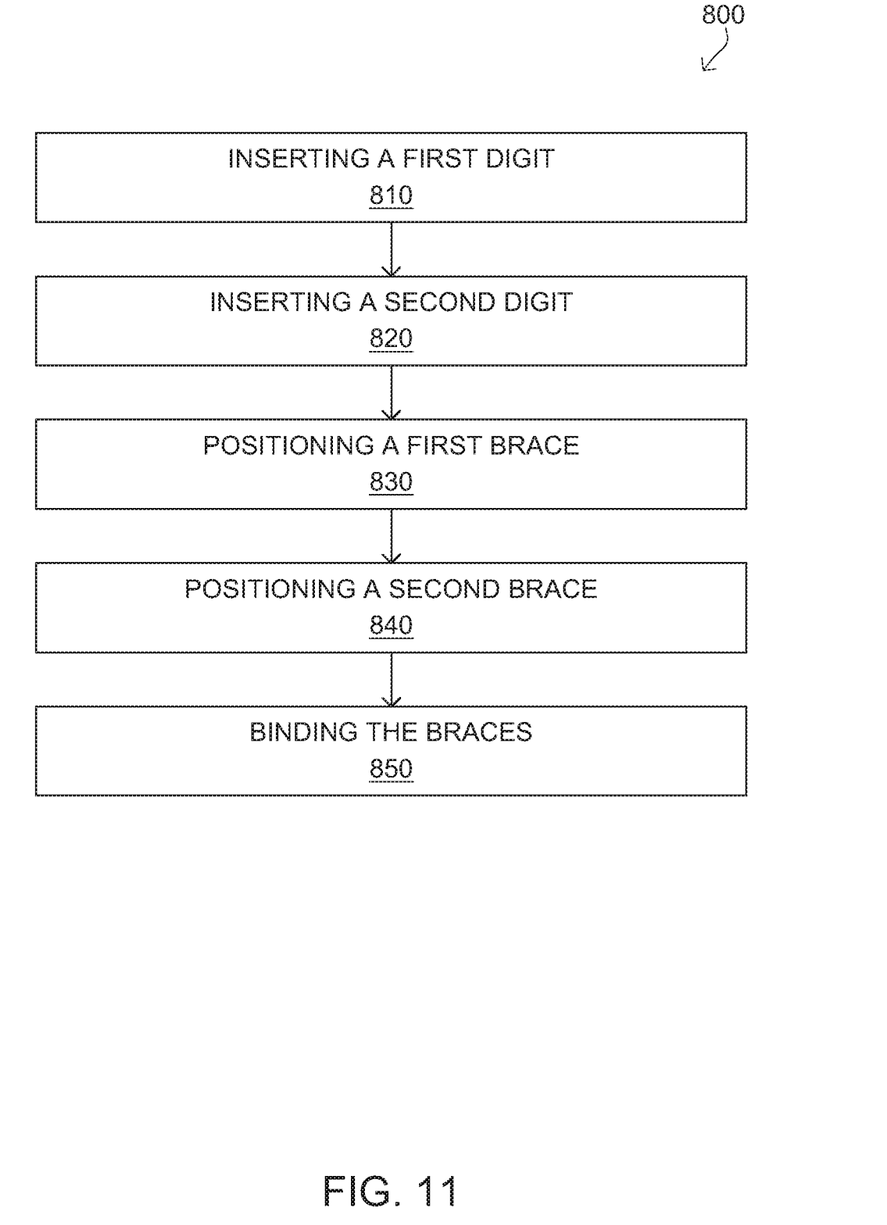
FIG. 11 is a flowchart showing a method of bracing a set of adjacent digits, according to one embodiment of the invention.

FIG. 11 shows a method 800 of bracing a set of adjacent digits. There is shown a step of inserting a first digit 810; a step of inserting a second digit 820; a step of positioning a first brace 830; a step of positioning a second brace 840; and a step of binding the braces 850. Accordingly, one may perform a syndactyly procedure on two adjacent digits for the health and benefit thereof.

The step of inserting a first digit includes inserting a first digit into a first arcuate member of a first brace. Such may be accomplished by threading the digit through an aperture through the arcuate member and/or by passing the body of the digit through a gap between ends of the arcuate member.

The step of inserting a second digit includes inserting a second digit (adjacent to the first) into a second arcuate member of the first brace, wherein the second arcuate member may be coplanar to, spaced from, and/or coupled to the first arcuate member. Such coupling may be by a top bridge member coupling a top region of the first arcuate member to a top region of the second arcuate member; and/or a bottom bridge member coupling a bottom region of the first arcuate member to a bottom region of the second arcuate member. Such may be accomplished by threading the digit through an aperture through the arcuate member and/or by passing the body of the digit through a gap between ends of the arcuate member.

The step of positioning the first brace includes positioning the first brace such that a rear face of the first brace, which rear face may have a narrowed portion, front-to-back, compared to a front face thereof, is oriented towards an adjacent joint of the digit and/or is oriented towards the palmar side of the knuckle. Such may be positioned adjacent any joint of any digit as desired. The illustrated braces would generally be positioned adjacent a joint of a finger of a hand, as they are shaped to better fit such a region. Other, similar, braces could be shaped to be comfortable to use with toes and/or for other digits, including the thumb, digits of individuals having differently shaped digits (e.g. due to birth defects, etc.) and/or digits of animals.

The step of positioning a second brace includes inserting adjacent fingers into the arcuate members of a second brace and then positioning a second brace on the first and second digits on an opposite side of the joint/knuckle with a rear face having a narrowed, front-to-back, portion facing the rear face of the first brace, such that the joint is flanked by the first and second braces and the first and second braces are back-to-back. Accordingly, when the joint bends, the narrow/thin portions of the arcuate members of both braces are in the palmar region of the knuckle between the two braces, which allows for greater flex and bend of that knuckle.

The step of binding the braces includes disposing an elastic band about the first brace, the elastic band sized such that it elastically couples to the brace. Such may also be accomplished using one or more wraps, straps or other similar rope/like structures and such may be coupled together by friction, adhesive, snaps, clips, and the like. It may be that one end of a wrap/strap is fixedly coupled to the brace and the other end may selectably couple once wrapped. It may be that the wrap may wrap about one or more portions of the hand beyond that covered by the brace and/or that a single wrap may wrap about and/or between more than one brace.

It is understood that the above-described embodiments are only illustrative of the application of the principles of the present invention. The present invention ay be embodied in other specific forms without departing rom its spirit or essential characteristics. The described embodiment is to be considered in all respects only as illustrative and not restrictive. The scope of the invention is, therefore, indicated by the appended claims rather than by the foregoing description. All changes which come within the meaning and range of equivalency of the claims are to be embraced within their scope.

For example, although the figures show only two arcuate members together in a brace, it is understood that additional arcuate members having similar form/shape/orientation may be present if it is desired to couple more than just two adjacent digits to each other. Accordingly, one could fix together three or more fingers/toes together as desired/needed.

Additionally, although the figures illustrate application of the described braces to fingers on a hand, it is understood that such may be applied to toes on a foot and that such may also be applied to similar appendages on animals.

It is expected that there could be numerous variations of the design of this invention. An example is that logo(s) may be disposed on one or more surfaces of the brace(s) and/or elastics/wraps/straps and/or that the faces of the braces may include thematic design elements.

Finally, it is envisioned that the components of the device may be constructed of a variety of materials, including but not limited to plastics, rubbers, silicones, natural fibers, synthetic fibers, metals, ceramics, and the like and combinations thereof.

Thus, while the present invention has been fully described above with particularity and detail in connection with what is presently deemed to be the most practical and preferred embodiment of the invention, it will be apparent to those of ordinary skill in the art that numerous modifications, including, but not limited to, variations in size, materials, shape, form, function and manner of operation, assembly and use may be made, without departing from the principles and concepts of the invention as set forth in the claims. Further, it is contemplated that an embodiment may be limited to consist of or to consist essentially of one or more of the features, functions, structures, methods described herein.

What is claimed is:

1. A multi-digit brace, comprising:
    a. a first arcuate member;
    b. a second arcuate member coplanar to, spaced from, and coupled to the first arcuate member by:
        i. a top bridge member coupling a top region of the first arcuate member to a top region of the second arcuate member; and
        ii. a bottom bridge member coupling a bottom region of the first arcuate member to a bottom region of the second arcuate member; and
    c. wherein the bottom region of each of the first and second arcuate members is thinner front-to-rear than a thickness of the top region;
    d. a band track extending about the top region, the bottom region, a left side region, and a right side region of the first and second arcuate members, the track bounded by a first raised barrier extending from and coplanar to a front face of the brace and bounded by a second raised barrier that extends from and coplanar to a rear face of the brace at the top region, wherein the band track is thinner front-to-rear in the bottom region than the thickness in the top region.

2. The multi-digit brace of claim 1, further comprising an elastic band removably coupled about the band track and elastically secured thereto.

3. The multi-digit brace of claim 2, further comprising an hourglass-shaped void between the first arcuate member and the second arcuate member.

4. The multi-digit brace of claim 3, wherein neither of the first arcuate member and the second arcuate member form a complete circle, thereby leaving a first gap between edges of the first arcuate member and a second gap between edges of the second arcuate member.

5. A multi-digit brace, comprising:
    a. a first arcuate member;
    b. a second arcuate member coplanar to and coupled to the first arcuate member by:
        i. a top bridge member coupling a top region of the first arcuate member to a top region of the second arcuate member; and
        ii. a bottom bridge member coupling a bottom region of the first arcuate member to a bottom region of the second arcuate member; and
    c. wherein the bottom region of each of the first and second arcuate members is thinner front-to-rear than a thickness of the top region;
    d. a band track extending about the top region, the bottom region, a left side region, and a right side region of the first and second arcuate members, the track bounded by a first raised barrier extending from and coplanar to a front face of the brace and bounded by a second raised barrier that extends from and coplanar to a rear face of the brace at the top region, wherein the band track is thinner front-to-rear in the bottom region than the thickness in the top region.

6. The multi-digit brace of claim 5, wherein neither of the first arcuate member and the second arcuate member form a complete circle, thereby leaving a first gap between edges of the first arcuate member and a second gap between edges of the second arcuate member.

7. The multi-digit brace of claim 6, wherein the first gap of the first arcuate member is disposed about a boundary between the right side region and the bottom region and the second gap of the second arcuate member is disposed about a boundary between the left side region and the bottom region.

8. The multi-digit brace of claim 5, further comprising an elastic band removably coupled about the band track and elastically secured thereto.

9. The multi-digit brace of claim 5, wherein the second arcuate member is spaced from the first arcuate member.

10. The multi-digit brace of claim 5, further comprising an hourglass-shaped void between the first arcuate member and the second arcuate member.

11. The multi-digit brace of claim 5, wherein at least one of the first arcuate member and the second arcuate member form a complete circle.

12. A multi-digit brace kit, comprising:
    a. a plurality of multi-digit braces, each brace including:
        iii. a first arcuate member;
        iv. a second arcuate member coplanar to, spaced from, and coupled to the first arcuate member by:
            1. a top bridge member coupling a top region of the first arcuate member to a top region of the second arcuate member; and
            2. a bottom bridge member coupling a bottom region of the first arcuate member to a bottom region of the second arcuate member; and v. wherein the bottom region of each of the first and second arcuate members is thinner front-to-rear than a thickness of the top region; and vi. a band track extending about the top region, the bottom region, a left side region, and a right side region of the first and second arcuate members, the track bounded by a first raised barrier extending from and coplanar to a front face of the brace and bounded by a second raised barrier that extends from and coplanar to a rear face of the brace at the top region, wherein the band track is thinner front-to-rear in the bottom region than the thickness in the top region;

b. a plurality of elastic bands, each sized to elastically couple about one of the plurality of braces.

13. The kit of claim 12, wherein the band track is not less wide than a band of the plurality of elastic bands.

14. The kit of claim 12, wherein a brace of the plurality of braces includes an hourglass-shaped void between the first arcuate member and the second arcuate member.

15. A method of bracing a set of adjacent digits, comprising the steps of:

a. inserting a first digit into a first arcuate member of a first brace;

b. inserting a second digit into a second arcuate member of the first brace, wherein the second arcuate member is coplanar to, spaced from, and coupled to the first arcuate member by a top bridge member coupling a top region of the first arcuate member to a top region of the second arcuate member; and a bottom bridge member coupling a bottom region of the first arcuate member to a bottom region of the second arcuate member; wherein a band track extends about the top region, the bottom region, a left side region, and a right side region of the first and second arcuate members, the track bounded by a first raised barrier extending from and coplanar to a front face of the brace and bounded by a second raised barrier that extends from and coplanar to a rear face of the brace at the top region, wherein the band track is thinner front-to-rear in the bottom region than a thickness in the top region;

c. positioning the first brace such that the rear face of the first brace, which the rear face has a narrowed portion, front-to-back, compared to the front face thereof, towards an adjacent joint of the first or second digit.

16. The method of claim 15, further comprising positioning a second brace on the first and second digits on an opposite side of the joint with a rear face having a narrowed, front-to-back, portion facing the rear face of the first brace, such that the joint is flanked by the first and second braces and the first and second braces are back-to-back.

17. The method of claim 15, further comprising disposing an elastic band about the first brace, the elastic band sized such that it elastically couples to the first brace.

\* \* \* \* \*